US006454738B1

(12) United States Patent
Tran et al.

(10) Patent No.: US 6,454,738 B1
(45) Date of Patent: Sep. 24, 2002

(54) METHODS FOR DELIVERING IN VIVO UNIFORM DISPERSED EMBOLIC COMPOSITIONS OF HIGH VISCOSITY

(75) Inventors: Chinh Ngoc Tran; Douglas Ray Hayman, both of Mission Viejo; Tom Whalen, II, Encinitas, all of CA (US)

(73) Assignee: Micro Therapeutics, Inc., Irvin, CA (US)

( * ) Notice: Subject to any disclaimer, the term of this patent is extended or adjusted under 35 U.S.C. 154(b) by 0 days.

(21) Appl. No.: 09/574,963

(22) Filed: May 19, 2000

Related U.S. Application Data

(60) Provisional application No. 60/135,222, filed on May 21, 1999.

(51) Int. Cl.[7] .............................................. A61M 31/00
(52) U.S. Cl. ............................ 604/49; 604/49; 604/30; 424/9.411; 424/78.37; 424/423; 424/484; 514/2; 514/21
(58) Field of Search ................... 604/49, 30; 424/423, 424/9.411, 428, 78.37; 514/2, 21

(56) References Cited

FOREIGN PATENT DOCUMENTS

| WO | WO 90/03768 | 4/1990 |
| WO | WO 98/04312 | 2/1998 |
| WO | WO 99/20326 | 4/1999 |

OTHER PUBLICATIONS

Mandai, et al., "Direct Thrombosis of Aneurysms with Cellulose Acetate Polymer", *J. Neurosurg.*, 77:497–500 (1992).
Kinugasa et al., "Direct Thrombosis of Aneurysms with Cellulose Acetate Polmer", *J. Neurosurg.*, 77:501–507 (1992).
Casarett and Doull's *Toxiclogy*, Amdur et al., Editors, Pergamon Press, New York, pp. 661–664 (1975).
Kinugasa, et al., "Early Treatment of Subarachnoid Hemorrhage After Preventing Rerupture of an Aneurysm", *J. Neurosurg.*, 83:34–41 (1995).
Kinugasa, et al., "Prophylatic Thrombosis to Prevent New Bleeding and to Delay Aneurysm Surgery", *Neurosurg.*, 36:661 (1995).
Taki, et al., "Selection and Combination of Various Edovascular Techniques in the Treatment of Giant Aneurysms", *J. Neurosurg.*, 77:37–42 (1992).

*Primary Examiner*—Christopher S. F. Low
*Assistant Examiner*—Hope A. Robinson
(74) *Attorney, Agent, or Firm*—Burns, Doane, Swecker & Mathis LLP

(57) ABSTRACT

Disclosed are novel techniques for embolizing blood vessels which are particularly suited for treating vascular lesions via catheter delivery of an embolic composition.

20 Claims, 1 Drawing Sheet

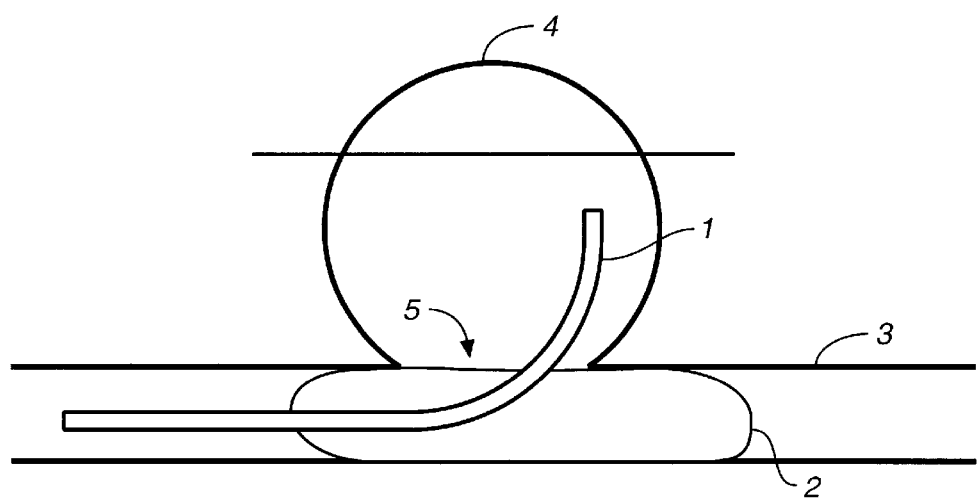
FIG._1

METHODS FOR DELIVERING IN VIVO UNIFORM DISPERSED EMBOLIC COMPOSITIONS OF HIGH VISCOSITY

CROSS REFERENCE TO RELATED APPLICATIONS

This application claims the benefit of U.S. Provisional Patent Application Serial No. 60/135,222 filed May 21, 1999, which application is incorporated herein by reference in its entirety.

BACKGROUND OF THE INVENTION

1. Field of the Invention

This invention is directed to methods for delivering in vivo uniform dispersed embolic compositions of high viscosity. These methods can be used in the treatment of aneurysms, AVM and high flow fistulas.

In one embodiment, the methods of this invention comprise heating to above about 40° C. while mixing a high viscosity composition comprising a biocompatible polymer, a biocompatible solvent and a biocompatible contrast agent. Heating and mixing is continued until a uniform suspension is formed and the heated suspension is then transferred to a catheter for vascular delivery.

2. References

The following publications are cited in this application as superscript numbers:

[1] Mandai, et al., "Direct Thrombosis of Aneurysms with Cellulose Acetate Polymer", *J. Neurosurg.*, 77:497–500 (1992)

[2] Kinugasa, et al., "Direct Thrombosis of Aneurysms with Cellulose Acetate Polymer", *J. Neurosurg.*, 77:501–507 (1992)

[3] Casarett and Doull's *Toxicology*, Amdur et al., Editors, Pergamon Press, New York, pp. 661–664 (1975)

[4] Greff, et al., U.S. patent application Ser. No. 08/507,863 for "Novel Compositions for Use in Embolizing Blood Vessels", filed Jul. 27, 1995

[5] Greff, et al., U.S. patent application Ser. No. 08/508,248 for "Cellulose Diacetate Compositions for Use in Embolizing Blood Vessels", filed Jul. 27, 1995

[6] Kinugasa, et al., "Early Treatment of Subarachnoid Hemorrhage After Preventing Rerupture of an Aneurysm", *J. Neurosurg.*, 83:34–41 (1995)

[7] Kinugasa, et al., "Prophylactic Thrombosis to Prevent New Bleeding and to Delay Aneurysm Surgery", *Neurosurg.*, 36:661 (1995)

[8] Taki, et al., "Selection and Combination of Various Endovascular Techniques in the Treatment of Giant Aneurysms", *J. Neurosurg.*, 77:3742 (1992)

[9] Evans, et al., U.S. patent application Ser. No. 08/655,822 for "Novel Compositions for Use in Embolizing Blood Vessels", filed May 31, 1996

[10] Dunn, et al., U.S. Pat. No. 4,938,763 for "Biodegradable In-Situ Forming Implants and Methods of Producing Same", issued Jul. 3, 1990

All of the above references are herein incorporated by reference in their entirety to the same extent as if each individual reference was specifically and individually indicated to be incorporated herein by reference in its entirety.

3. State of the Art

Embolization of blood vessels is conducted for a variety of purposes including the treatment of tumors, the treatment of lesions such as aneurysms, uncontrolled bleeding and the like.

Embolization of blood vessels is preferably accomplished via catheter techniques which permit the selective placement of the catheter at the vascular site to be embolized. In this regard, recent advancements in catheter technology as well as in angiography now permit neuroendovascular intervention including the treatment of otherwise inoperable lesions. Specifically, development of microcatheters and guide wires capable of providing access to vessels as small as 1 mm in diameter allows for the endovascular treatment of many lesions.

Embolic compositions heretofore disclosed in the art include those comprising a biocompatible polymer, a biocompatible solvent and a contrast agent which allowed visualization of the in vivo delivery of the composition via fluoroscopy.[1-8] Such compositions typically contain no more than about 8 weight percent of biocompatible polymer based on the weight of the total composition.

Endovascular treatment regimens preferably include the use of a water insoluble, radiopaque contrast agent in the embolic compositions in order that the physician can visualize delivery of the composition to the vascular site via conventional techniques such as fluoroscopy.[1-8] Additionally, the use of water insoluble contrast agents is beneficial during post treatment procedures to visualize the embolized mass during, for example, surgery or to monitor the disease condition and/or retreatment purposes.

Visualization is particularly necessary when using catheter delivery techniques in order to ensure both that the composition is being delivered to the intended vascular site and that the requisite amount of composition is delivered. The latter requirement is particularly critical in the treatment of aneurysms where only the aneurysm sac is intended to be filled while leaving the adjoining blood vessel unaffected.

Accordingly, in such treatments, the amount of embolic composition delivered is selected to substantially fill but not overflow the aneurysm sac. If less than this amount of embolic composition is delivered to the aneurysm sac, the patient will be left with an active aneurysm which, in some cases, may grow/enlarge over time. If more than this amount of embolic composition is delivered, the composition will overflow into the adjoining blood vessel which can then embolize this blood vessel as well as the aneurysm. In the case where the affected blood vessel is in or leads to a critical body organ, e.g., the brain, damage due to blood flow reduction or cessation can result in severe patient disability or death.

When delivered by catheter, the embolic compositions preferably comprise a biocompatible solvent, a biocompatible polymer and the water insoluble contrast agent. The biocompatible solvent is miscible or soluble in blood or other body fluid and also solubilizes the biocompatible polymer during delivery. The biocompatible polymer is selected to be soluble in the biocompatible solvent but insoluble in blood or other body fluid. The water insoluble contrast agent is suspended in the composition and, as above, permits the physician to fluoroscopically visualize catheter delivery of this composition. Upon contact with the blood or other body fluid, the biocompatible solvent dissipates from the embolic composition whereupon the biocompatible polymer precipitates in the presence of the water insoluble contrast agent and embolizes the blood vessel.

Notwithstanding the benefits associated with the use of such embolic compositions in treating aneurysms and other vascular disorders, in vivo these compositions formed coherent masses which often suffer from solidification and formation of a coherent mass distal from the point of ejection from the catheter. That is to say that upon ejection of the embolic composition in a vascular site, the coherent mass subsequently formed was often distal and not proximate the ejection port of the catheter. Moreover, upon solidification, the solid mass formed was often linear in shape (i.e., having a "string shape").

In many circumstances, a contiguous or ball shape precipitate formed at the ejection port is desired (e.g., to fill an aneurysm sac). Distal solidification of a string shape precipitate makes site specific delivery of the solid mass in the vasculature difficult. As is apparent, site specific delivery of the solid mass is essential for treatment of vascular disorders such as aneurysms. Solidification at points distal to the ejection port, as is common in string shape precipitates, can result in the solid mass forming not in the aneurysm sac but in the artery attendant the aneurysm. Such a string shape precipitate is more prone to fragmentation which can lead to embolization of this artery and possible incapacitation or death of the patient. Moreover, such fragmentation can lead to particles or fragments being "washed" downstream and lodging at undesired locations in the vasculature.

To address this problem, U.S. patent application Ser. No. 09/574,379, concurrently filed herewith and entitled "Novel High Viscosity Embolizing Compositions" discloses that the use of high viscosity embolic compositions comprising a biocompatible polymer, a biocompatible solvent and a contrast agent permits site specific delivery of these compositions to the vascular site. The contents of this application are incorporated herein by reference in its entirety.

A problem has arisen with the use of such high viscosity compositions. Specifically, the high viscosity of the biocompatible polymer/biocompatible solvent mixture makes it difficult to form a uniform suspension when combined with the water insoluble contrast agent and that such high viscosity compositions are difficult to deliver through a catheter. Contrarily, the delivery of such a uniform suspension is critical for the ability of the clinician to consistently view the delivery of the composition in vivo.

SUMMARY OF THE INVENTION

This invention is directed to novel methods for delivering in vivo uniform suspensions of high viscosity embolic compositions comprising a water insoluble contrast agent.

Specifically, this invention is directed to the discovery that facile in vivo delivery of a uniform suspension of embolic composition can be achieved by mixing the embolic compositions at a temperature of above about 40° C. which ensures formation of a uniform suspension and then transferring this heated composition under conditions wherein the temperature of this composition is above room temperature and preferably above about 40° C. into the catheter for in vivo delivery. Surprisingly, the heated composition maintains both a uniform suspension and ease of delivery during catheter injection into a vascular site in a mammal and, when ejected at the distal end of the catheter, there is no evidence of trauma to this site.

Without being limited to any theory, it is believed that transferring the heated embolic composition to the catheter allows this composition to retain a sufficiently low viscosity during delivery in vivo such that this delivery is facilitated. It is further believed that during traversal through the catheter, the temperature of the embolic composition equilibrates with the body temperature such that at the ejection port, the embolic composition does not cause any significant trauma to the vascular site. In this regard, a sufficient length of catheter is employed to allow the temperature of the embolic composition to equilibrate with the mammal's body temperature. Preferably, the catheter is at least 50 cm in length and, more preferably, is as least 75 cm in length.

Accordingly, in one of its method aspects, the invention is directed to a method for embolizing a vascular site comprising an opening that is in communication with a vascular vessel by delivering via a catheter into said vascular site an embolic composition comprising (1) a biocompatible polymer, (2) a biocompatible solvent which solubilizes said polymer, and (3) water insoluble contrast agent which is suspended in said composition wherein said composition has a viscosity of at least 150 cSt at 40° C., said method comprises:
(a) heating and mixing the embolic composition at a temperature of at least 40° C. to form a uniform suspension;
(b) positioning the distal end of a delivery catheter at the vascular site to be embolized;
(c) transferring the composition prepared in (a) above to the delivery catheter under conditions wherein the temperature of the composition is above room temperature and preferably above 40° C.; and
(d) injecting said composition into said vascular site under conditions wherein the temperature of said composition at the ejection port is in substantial equilibrium with the body temperature of said mammal and further wherein sufficient amounts of said composition are injected under conditions which embolize said vascular site.

In a preferred embodiment, equilibration of the temperature of the embolic composition at the ejection port with the body temperature of the mammal is achieved by use of a catheter which is at least 50 cm in length and, more preferably, is as least 75 cm in length.

In another embodiment particularly suited for treating aneurysms, the methods of this invention preferably employ a flow arresting device at the vascular site such that the activated device substantially seals the opening and does not occlude the delivery catheter. Preferably, the flow arresting device comprises an inflatable balloon which upon inflation has a diameter that is equal to or greater than the inner diameter of the vascular vessel.

In one embodiment, the inflated balloon has a diameter that is about 100% to 130% of the inner diameter of the vascular vessel, and more preferably about 115% particularly when employed in the neurovascular system. In another embodiment, after step (d), the balloon is deflated until its diameter is about 10% to 90% of the inner diameter of the vascular vessel. Preferably the diameter is about 20–25%. In a particularly preferred embodiment, the process of inflation, delivery of embolic composition and deflation is repeated as necessary to effect embolization of the vascular site.

It is contemplated that a flow arresting device (i.e., a device that either controls or reduces blood flow through a vessel) can be used in treating of other neural and peripheral vascular disorders including, for example, AVM's, AVF's and the like.

Accordingly, in another of its method aspects, this invention is directed to a method for embolizing a vascular site comprising an opening that is in communication with a vascular vessel by delivering via a catheter into said vascular site an embolic composition comprising (1) a biocompatible polymer; (2) a biocompatible solvent which solubilizes said polymer; and (3) water insoluble contrast agent which is suspended in said composition wherein said composition has a viscosity of at least 150 cSt at 40° C., said method including the steps of:
(a) heating and mixing the embolic composition at a temperature of at least 40° C. under conditions which form a uniform suspension;

(b) positioning the distal end of a delivery catheter into the vascular site to be embolized;

(c) positioning a flow arresting device at the vascular site to be embolized;

(d) connecting the delivery catheter to the composition prepared in (a) above under conditions wherein the temperature of the composition is above room temperature and preferably above 40° C.;

(e) activating the flow arresting device at the vascular site to be embolized such that the activated device substantially arrests blood flow through the vascular site to be embolized but does not occlude the delivery catheter;

(f) injecting said composition into said vascular site under conditions wherein the temperature of said composition at the ejection port is in substantial equilibrium with the body temperature of said mammal;

(g) deactivating the flow arresting device to permit sufficient blood flow through said vasculature to be embolized such that removal of the biocompatible solvent is facilitated and oxygenated blood is delivered to the tissue distal to said flow arresting device; and (h) repeating steps (e)–(g) as necessary to effect embolization of said vascular site.

BRIEF DESCRIPTION OF THE DRAWINGS

FIG. 1 illustrates a blood vessel having a catheter placed therein for the purpose of delivering an embolic composition thereto.

DETAILED DESCRIPTION OF THE INVENTION

This invention is directed to novel compositions for embolizing blood vessels which are particularly suited for treating vascular lesions via catheter delivery of the composition.

However, prior to discussing this invention in further detail, the following terms will first be defined:

The term "embolizing" refers to a process wherein a material is injected into a blood vessel which, in the case of, for example, aneurysms, fills or plugs the aneurysm sac and/or encourages clot formation so that blood flow into the aneurysm ceases, in the case of high flow AVM's forms a plug or clot to control/reroute blood flow to permit proper tissue perfusion, and, in the case of a vascular site, fills the vascular site to prevent blood flow there through. Embolization of the blood vessel is, therefore, important in preventing/con-trolling bleeding due to lesions (e.g., organ bleeding, gastrointestinal bleeding, vascular bleeding as well as bleeding associated with an aneurysm). In addition, embolization can be used to ablate diseased tissue (e.g., tumors, etc.) by cutting off its blood supply.

The term "biocompatible polymer" refers to polymers which, in the amounts employed, are non-toxic and substantially non-immunogenic when used internally in the patient and which are substantially insoluble in the body fluid of the mammal. The biocompatible polymer can be either biodegradable or, preferably, non-biodegradable.

Biodegradable polymers are disclosed in the art. For example, Dunn, et al.[10] discloses the following examples of biodegradable polymers: linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), polyvinylpyrrolidone, polyethylene glycol, polyhydroxycellulose, chitin, chitosan, and copolymers, terpolymers and combinations thereof. Other biodegradable polymers include, for example, gelatin, collagen, etc.

Suitable non-biodegradable biocompatible polymers include, by way of example, cellulose acetates[2,6-7] (including cellulose diacetate[5]), ethylene vinyl alcohol copolymers[4,8], hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof[9].

Preferably, the biocompatible polymer employed does not cause an adverse inflammatory reaction when employed in vivo. The particular biocompatible polymer employed is selected relative to the viscosity of the resulting polymer solution, the solubility of the biocompatible polymer in the biocompatible solvent, and the like. For example, the selected biocompatible polymer should be soluble in the amounts employed in the selected biocompatible solvent and the resulting composition should have a viscosity suitable for in vivo delivery by the methods of this invention.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by merely adjusting the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. As is apparent to one skilled in the art, with all other facts being equal, copolymers having a lower molecular weight will impart a lower viscosity to the composition as compared to higher molecular weight copolymers. Accordingly, adjustment of the viscosity of the composition as necessary for catheter delivery can be readily achieved by merely adjusting the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous environment (e.g., blood or tissue). In a particularly preferred embodiment, the copolymers employed herein comprise a mole percent of ethylene of from about 25 to about 60 and a mole percent of vinyl alcohol of from about 40 to about 75. These compositions provide for requisite precipitation rates suitable for use in the methods described therein.

The term "contrast agent" refers to a biocompatible radiopaque material capable of being monitored during injection into a mammalian subject by, for example, radiography. In the methods of this invention, the contrast agent is water insoluble (i.e., has a water solubility of less than 0.01 mg/ml at 20° C.).

Examples of water insoluble contrast agents include tantalum, tantalum oxide, and barium sulfate, each of which is commercially available in the proper form for in vivo use including a preferred particle size of about 10 $\mu$m or less. Other water insoluble contrast agents include gold, tungsten, and platinum powders.

The term "biocompatible solvent" refers to an organic material liquid at least at body temperature of the mammal in which the biocompatible polymer is soluble and, in the amounts used, is substantially non-toxic. Suitable biocompatible solvents include, by way of example, ethyl lactate, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

Compositions

The polymer compositions employed in this invention are prepared by conventional methods whereby each of the components is added and the resulting composition mixed.

For example, these compositions can be prepared by adding sufficient amounts of a biocompatible polymer, a biocompatible contrast agent, and a biocompatible solvent which solubilizes said biocompatible polymer wherein the viscosity of this composition is at least about 150 cSt at 40° C. If necessary, gentle heating and stirring can be used to effect dissolution of the biocompatible polymer into the biocompatible solvent, e.g., 12 hours at 50° C.

The viscosity of the composition is controlled either by the amount of polymer employed and/or its molecular weight. For example, high viscosity compositions which employ low concentrations of polymer can be achieved by use of very high molecular weight biocompatible polymers (e.g., average molecular weight greater than 250,000). Such factors are well known in the art. In any event, the compositions employed in the methods of this invention have a viscosity of at least about 150 cSt at 40° C., preferably at least about 200 cSt at 40° C., and more preferably at least about 500 cSt at 40° C. Preferably, the viscosity ranges from about 200 to 40,000 cSt at 40° C., more preferably from about 500 to 40,000 cSt at 40° C. In another embodiment, the viscosity ranges from about 500 to 5000 cSt at 40° C.

Preferred compositions include those comprising:

(a) a biocompatible polymer at a concentration of from about 2 to 50 weight percent;

(b) a biocompatible contrast agent at a concentration of from about 10 to about 40 weight percent; and (c) a biocompatible solvent from about 10 to 88 weight percent wherein the weight percent of the biocompatible polymer, contrast agent and biocompatible solvent is based on the total weight of the complete composition and further wherein the composition has a viscosity of at least about 150 and more preferably at least about 200 cSt at 40° C.

Preferably, the concentration of the polymer ranges from 6 to 50 weight percent and more preferably 8 to 30 weight percent.

Preferably, the composition will comprise from about 10 to about 40 weight percent of the contrast agent and more preferably from about 20 to about 40 weight percent and even more preferably about 30 weight percent. Insofar as water insoluble contrast agents are not soluble in the biocompatible solvent, stirring is employed to effect homogeneity of the resulting suspension for compositions employing such contrast agents.

Other high viscosity embolic compositions comprising a biocompatible polymer, a biocompatible solvent and a contrast agent are disclosed in U.S. patent application Ser. No. 09/574,379, filed concurrently herewith and entitled "Novel High Viscosity Embolizing Compositions". The contents of this application are incorporated herein by reference in its entirety.

In order to enhance formation of a homogenous suspension, the particle size of water insoluble contrast agents is preferably maintained at about 10 $\mu$m or less and more preferably at from about 1 to about 5 $\mu$m (e.g., an average size of about 2 $\mu$m).

The particular order of addition of components to the biocompatible solvent is not critical and stirring of the resulting solution or suspension is conducted as necessary to achieve homogeneity of the composition. Preferably, mixing/stirring of the composition is conducted under an anhydrous atmosphere at ambient pressure. The resulting composition is heat sterilized and then stored preferably in sealed bottles or vials until needed.

Each of the polymers recited herein is commercially available but can also be prepared by methods known in the art. For example, polymers are typically prepared by conventional techniques such as radical, thermal, UV, $\gamma$ irradiation, or electron beam induced polymerization employing, as necessary, a polymerization catalyst or initiator to provide for the polymer composition. The specific manner of polymerization is not critical and the polymerization techniques employed do not form a part of this invention.

In order to maintain solubility in the biocompatible solvent, the polymers described herein are preferably not cross-linked.

Methods

The compositions described above can then be employed in methods for the catheter assisted embolization of mammalian blood vessels. In such methods, a homogenous suspension of the composition must be used in order to consistently visualize the contrast agent via fluoroscopy during injection. However, during storage of the compositions described above, the water insoluble contrast agent often falls from suspension and, accordingly, prior to use, a homogenous suspension must be regenerated.

Because of their high viscosities, mixing these compositions at ambient conditions does not readily form a homogenous suspension. Accordingly, in this invention, a uniform suspension is achieved by mixing of the compositions at a temperature above about 40° C., preferably from above about 40° C. to about 90° C., and more preferably from about 50° C. to about 70° C. The particular temperature employed should be sufficiently high to ensure adequate mixing of the composition.

In a particularly preferred embodiment, the composition is heated for a period of time from at least about 3 to about 20 minutes and preferably from about 5–10 minutes to facilitate formation of a uniform suspension. In some cases, the formation of a uniform suspension requires that the heated composition be placed in a suitable mixer, e.g., vortex mixer, and is mixed until the suspension is homogeneous. In this case, after formation of the homogenous suspension via the mixer, the composition is preferably reheated to a temperature of from above about 40° C. to about 90° C. and preferably from about 50° C. to about 70° C. The specific temperature employed for heating is selected relative to the biocompatible solvent and biocompatible polymer employed. Such selections are well within the skill of the art.

In either case, the heated composition is then transferred preferably via a syringe and delivered into the catheter under conditions wherein the temperature of the composition is above room temperature and preferably above about 40° C. In one preferred embodiment, the conditions which effect such transfer are rapid transfer (e.g., transfer occurs within 2 minutes of heating cessation) of the composition to the catheter.

A sufficient amount of this composition is introduced into the selected blood vessel via a catheter delivery means under fluoroscopy so that upon precipitation of the polymer, the blood vessel is embolized. The particular amount of composition employed is dictated by the total volume of the vasculature to be embolized, the concentration of polymer in the composition, the rate of precipitation (solids formation) of the polymer, etc. Such factors are well within the skill of the art.

The catheter employed is of particular importance due to the nature and temperature of the composition. First, the catheter must be made of materials compatible with both the temperature of the composition as well as the components used in the composition. That is to say that the polymeric catheter components will not readily degrade in the composition either due to heat and/or the chemical nature of the composition. In this regard, it is preferred to use polyethylene in the catheter components because of its inertness in the presence of the embolic composition described herein. Other materials compatible with the compositions can be readily determined by the skilled artisan and include, for example, other polyolefins, fluoropolymers (e.g., Teflon™), silicone, etc.

Second, the length of the catheter employed must be sufficient to allow the temperature of the composition to equilibrate with the mammal's body temperature prior to ejection from the ejection port. Preferably, the catheter length is at least 50 cm and, more preferably at least 75 cm. The total length of the catheter is, of course, dependent upon the point of insert (typically the femoral artery), the vascular site to be embolized and the vasculature which must be traversed to reach that site. Such factors are well within the skill of the art. However, preferably, the maximum length of the catheter is typically about 200 cm.

The preferred delivery techniques will be described in treating aneurysm but it is understood that the techniques are applicable for treating vascular sites in general. As shown in FIG. 1, vascular site 3 has an opening 5 that forms the aneurysm. The top of the sac 4 is typically referred as the fundus 4 and the base of the sac at the opening is the neck.

Standard procedures can be employed to position the distal (i.e., tip) of delivery catheter 1 into the sac. One method of securing the delivery catheter 1 in place during the embolization procedure is to employ an occluding or flow arresting device such as inflatable balloon 2.

The proximal end of the delivery catheter is connected to one or more syringes. Multiple syringes each containing different and heated embolic compositions can be employed to load the composition into the channel of the delivery catheter.

Sufficient amounts of the heated embolic compositions are then delivered to the aneurysm under fluoroscopy such as to fill the aneurysm sac. Traversal of the heated composition through the catheter which is positioned through the vasculature which acts as a heat sink for the catheter results in the ejected composition being in substantial equilibrium with the body temperature of the mammal. That is to say that the composition when delivered is sufficiently approximate body temperature that little or no thermal trauma occurs upon injection. Preferably the temperature of the composition is approximately ±2° C. of body temperature at the ejection port and more preferably ±1° C. At this temperature, no significant thermal trauma to the vascular site occurs upon ejection of this composition.

It is understood, of course, that the temperature of the composition ejected from the distal end of the catheter will depend upon the composition's initial temperature, the rate of heat loss from the composition, the length of the catheter, the ejection rate of the composition from the catheter, etc. Preferably, the composition's ejection rate is approximately less than 1 cc/minute which, when coupled with catheter lengths of at least about 50 cm and an initial temperature of no more than 90° C., allow for delivery of compositions in substantial equilibrium with body temperature. Of course, the particular flow rate, etc. will be selected by the clinician bearing in mind the necessity to have the ejected composition in substantial equilibrium with body temperature.

In addition to the above, the heated nature of the composition allows for more facile delivery through the catheter and, in turn, this results in substantially more uniform delivery of the composition by the clinician than would be achieved by employing such high viscosity compositions maintained at room temperature.

When delivered by catheter, preferred delivery techniques include those set forth in concurrently filed U.S. patent application Ser. No. 09/574,500, entitled "Methods for Embolizing Vascular Sites With an Embolizing Composition" and which application is incorporated herein by reference in its entirety.

In another embodiment, the catheter employs an interface device which connects to the syringe to create a blunt interface between a DMSO composition not containing either a biocompatible polymer or a contrast agent and the embolic composition described herein. Such devices are disclosed in U.S. patent application Ser. No. 09/574,392, concurrently filed herewith, and entitled "Interface Needle and Method for Creating a Blunt Interface Between Delivered Liquids" which is incorporated herein by reference in its entirety.

Still further, in some cases, the catheter delivery means employs threaded syringes as described in U.S. Provisional Patent Application Serial Nos. 60/135,289 and 60/135,287, entitled "THREADED SYRINGE" and entitled "SCREW SYRINGE WITH FORCE RELEASE MECHANISM", both of which were filed on May 21, 1999. Both of these applications are incorporated herein by reference in their entirety.

When high pressure is employed to effect delivery, the catheter preferably is rated to 100 psi use pressure to ensure against rupture.

Utility

The methods, devices, and compositions described herein are useful in embolizing mammalian blood vessels which, in turn, can be used to prevent/control bleeding (e.g., organ bleeding, gastrointestinal bleeding, vascular bleeding, bleeding associated with an aneurysm) or to ablate diseased tissue (e.g., tumors, etc.). Accordingly, the invention finds use in human and other mammalian subjects requiring embolization of blood vessels.

It is contemplated that the compositions can be employed as a carrier for a compatible pharmaceutically active compound wherein this compound is delivered in vivo for subsequent release. Such compounds include by way of example only antibiotics, anti-inflammatory agents, chemotherapeutic agents, anti-angiogenic agent, and the like.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

| | |
|---|---|
| cc = | cubic centimeters |
| cSt = | centistokes |
| DMSO = | dimethylsulfoxide |
| EVOH = | ethylene vinyl alcohol copolymer |
| g = | gram |
| mL = | milliliter |
| mm = | millimeter |
| $\mu$m = | micron |

Example 1

This example illustrates the preparation of compositions of this invention having a high viscosity. Specifically, an EVOH polymer composition was prepared as follows:

17.5 weight % EVOH polymer having a 48 mole % ethylene, with a molecular weight of approximately 136,000

30 weight % micronized tantalum 52.5 weight % anhydrous DMSO

Viscosity=approximately 1100 cSt at 40° C.

After dissolution of the polymer at 50° C. in DMSO with stirring, micronized tantalum (average size 3 $\mu$m) was then added. The resulting composition was then heated for approximately 5 minutes at 70° C. in a heated block, removed and then shaken in a vortex mixer for approximately 20 minutes at room temperature to disperse the insoluble tantalum and to provide for a uniform suspension of the tantalum in the polymer/solvent solution. The composition was replaced into the 70° C. heated block and rewarmed for a minimum of 10 minutes before filling a syringe and injection.

Example 2

An experimental side wall venous pouch aneurysm was created in the left carotid artery of a 25 kg juvenile domestic swine. A femoral access was made immediately thereafter and a microcatheter (MicroTherapeutics Rebar Microcatheter ™) was placed near the aneurysm site with the aid of a 0.014 inch guide wire (Microtherapeutics Silver Speed ™). Through another femoral access, a microballoon catheter (Microtherapeutics Equinox microballoon catheter) was also placed at the aneurysm site.

The microcatheter was then placed through the aneurysm neck into the aneurysm sac at least one third toward the fundus of the aneurysm. The microballoon bridged the neck of the aneurysm. The microcatheter was flushed with 5 mL of saline and then primed with 0.25 cc of DMSO. A threaded syringe filled with the composition of Example 1 (as described above) was then connected to an interface needle device (as described above). The threaded syringe interface needle device assembly was then connected to the microcatheter.

The balloon was then inflated to completely occlude blood flow through the carotid artery and seal the aneurysm neck. Approximately 0.2 mL of the composition of Example 1 was injected at a steady rate not exceeding 0.1 mL per minute. The composition was kept warm at approximately 40° C. during this process.

The balloon was deflated for two minutes to allow the solvent to dissipate. The balloon was then re-inflated and an additional 0.2 mL of the composition was, again injected through the delivery catheter with use of the screw syringe device. The balloon was allowed to remain inflated for 5 minutes. The process of balloon inflation, injection of composition and balloon deflation was repeated until the aneurysm was completely filled to the neck as determined by fluoroscopy. The delivery microcatheter was then withdrawn, the balloon was deflated and the microballoon catheter withdrawn.

From the foregoing description, various modifications and changes in the above described methods will occur to those skilled in the art. All such modifications coming within the scope of the appended claims are intended to be included therein.

What is claimed is:

1. A method for embolizing a vascular site, said method comprising:
    (a) preparing an embolic composition comprising (1) a biocompatible polymer, (2) a biocompatible solvent which solubilizes said polymer, and (3) a water insoluble contrast agent which is suspended in said composition, wherein said embolic composition has a viscosity of at least 150 centistokes at 40° C.,
    (b) heating and mixing the embolic composition to at least 40° C. to form a uniform suspension,
    (c) transferring the heated embolic composition to a delivery catheter having a proximal end and a distal end, wherein the distal end of the delivery catheter is positioned at the vascular site to be embolized, and
    (d) injecting the heated embolic composition into said vascular site in sufficient amounts to embolize said vascular site.

2. The method according to claim 1 wherein the composition transferred in (c) is maintained at a temperature above 40° C.

3. The method according to claim 1 wherein, prior to (d) above, a blood flow attenuating device is inserted immediately upstream the ejection port of said catheter.

4. The method according to claim 3 wherein said blood flow attenuating device is an inflatable microballoon which permits both normal and attenuated blood flow depending upon whether the microballoon is deflated or inflated.

5. The method according to claim 1, wherein said composition has a viscosity of at least 200 centistokes at 40° C.

6. The method according to claim 5, wherein said composition has a viscosity of at least 500 centistokes at 40° C.

7. The method according to claim 6, wherein said composition has a viscosity of from at least 500 to 5,000 centistokes at 40° C.

8. The method according to claim 1, wherein the concentration of biocompatible polymer employed in said composition is from 6 to 50 weight percent.

9. The method according to claim 8, wherein the concentration of biocompatible polymer employed in said composition is from 8 to 30 weight percent.

10. The method according to claim 1 wherein said biocompatible solvent is selected from the group consisting of ethyl lactate, dimethylsulfoxide, ethanol and acetone.

11. The method according to claim 10 wherein said biocompatible solvent is dimethylsulfoxide.

12. The method according to claim 1 wherein said water insoluble contrast agent is selected from the group consisting of tantalum, tantalum oxide, tungsten and barium sulfate.

13. The method according to claim 12 wherein said contrast agent is tantalum.

14. The method according to claim 1 wherein said biocompatible polymer is a non-biodegradable, biocompatible polymer.

15. The method according to claim 14 wherein said non-biodegradable, biocompatible polymer is selected from the group consisting of cellulose acetates, ethylene vinyl alcohol copolymers, hydrogels, polyacrylonitrile, polyvinylacetate, cellulose acetate butyrate, nitrocellulose, copolymers of urethane/carbonate, copolymers of styrene/maleic acid, and mixtures thereof.

16. The method according to claim 15 wherein said biocompatible polymer is an ethylene and vinyl alcohol copolymer.

17. The method according to claim 1 wherein said biocompatible polymer is a biodegradable, biocompatible polymer.

18. The method according to claim 1 wherein said catheter has a length of at least 50 cm.

19. A method for embolizing a vascular site, said method comprising:

(a) preparing an embolic composition comprising (1) a biocompatible polymer, (2) a biocompatible solvent which solubilizes said polymer, and (3) a water insoluble contrast agent which is suspended in said composition, wherein said embolic composition has a viscosity of at least 150 centistokes at 40° C., (b) heating and mixing the embolic composition to at least 40° C. to form a uniform suspension, (c) positioning the distal end of a delivery catheter having a proximal end and a distal end into the vascular site to be embolized, (d) positioning a flow arresting device at the vascular site to be embolized, (e) connecting the delivery catheter to the embolic composition prepared in (a) above under conditions wherein the temperature of the composition is above room temperature, (f) activating the flow arresting device at the vascular site to be embolized such that the activated device reduces blood flow through the vascular site to be embolized but does not occlude the delivery catheter, (g) injecting said composition into said vascular site under conditions wherein the temperature of said composition at the ejection port is in equilibrium with the body temperature of said mammal, (h) deactivating the flow arresting device to permit sufficient blood flow through said vasculature to be embolized such that removal of the biocompatible solvent is facilitated and oxygenated blood is delivered to the tissue distal to said flow arresting device, and (i) repeating steps (f)–(h) as necessary to effect embolization of said vascular site.

20. The method according to claim 19 wherein the composition transferred in (e) is maintained at a temperature above 40° C.

* * * * *